(12) United States Patent
Baumgart

(10) Patent No.: US 10,297,038 B2
(45) Date of Patent: May 21, 2019

(54) DETERMINATION AND PRESENTATION OF FLOW TRANSIT CURVES

(71) Applicant: Siemens Medical Solutions USA, Inc., Malvern, PA (US)

(72) Inventor: John Baumgart, Hoffman Estates, IL (US)

(73) Assignee: Siemens Healthcare GmbH, Erlangen (DE)

( * ) Notice: Subject to any disclaimer, the term of this patent is extended or adjusted under 35 U.S.C. 154(b) by 23 days.

(21) Appl. No.: 15/474,753

(22) Filed: Mar. 30, 2017

(65) Prior Publication Data

US 2018/0279984 A1    Oct. 4, 2018

(51) Int. Cl.
| | |
|---|---|
| *G06K 9/00* | (2006.01) |
| *G06T 7/70* | (2017.01) |
| *A61B 6/00* | (2006.01) |
| *G06T 7/00* | (2017.01) |
| *G06T 11/20* | (2006.01) |
| *A61B 6/04* | (2006.01) |

(52) U.S. Cl.
CPC .............. *G06T 7/70* (2017.01); *A61B 6/4441* (2013.01); *A61B 6/481* (2013.01); *A61B 6/504* (2013.01); *A61B 6/5211* (2013.01); *G06T 7/0012* (2013.01); *G06T 11/20* (2013.01); *A61B 6/0464* (2013.01); *A61B 6/461* (2013.01); *G06T 2207/10116* (2013.01); *G06T 2207/30101* (2013.01)

(58) Field of Classification Search
CPC ........ A61B 6/5205; A61B 6/461; A61B 6/481; G06T 2207/10116; G06T 2207/301; G06T 7/70; G06T 7/0012; G06T 11/20
See application file for complete search history.

(56) References Cited

U.S. PATENT DOCUMENTS

| | | | |
|---|---|---|---|
| 4,813,762 A * | 3/1989 | Leger | ................... H01S 5/4062 |
| | | | 359/565 |
| 5,583,902 A * | 12/1996 | Bae | ........................ G16H 50/50 |
| | | | 378/8 |
| 6,377,835 B1 | 4/2002 | Schoenberg et al. | |
| 7,756,562 B2 | 7/2010 | Kimura | |
| 8,848,996 B2 | 9/2014 | Baumgart | |
| 9,320,486 B2 | 4/2016 | Baumgart | |
| 2009/0208071 A1* | 8/2009 | Nishimura | ............. A61B 1/041 |
| | | | 382/128 |
| 2009/0316970 A1* | 12/2009 | Kemper | ............... G06K 9/6223 |
| | | | 382/131 |
| 2010/0053209 A1 | 3/2010 | Rauch et al. | |

(Continued)

*Primary Examiner* — Amara Abdi

(57) ABSTRACT

A system and method includes reception of an indication of a region of interest of a plurality of image frames, determination of a first set of pixel locations of the region of interest which depict blood vessels, determination of a second set of pixel locations of the region of interest which depict non-vessel tissue, determination, for each of the plurality of the image frames, of a first contrast medium concentration corresponding to the first set of pixel locations, determination, for each of the plurality of the image frames, of a second contrast medium concentration corresponding to the second set of pixel locations, and display of a visualization depicting a first contrast medium concentration and a second medium concentration with respect to the respective time of each of the plurality of the image frames.

19 Claims, 8 Drawing Sheets

(56) References Cited

U.S. PATENT DOCUMENTS

| | | | |
|---|---|---|---|
| 2010/0253342 A1* | 10/2010 | Kimura | A61B 5/0275 324/309 |
| 2013/0182120 A1* | 7/2013 | Nakajima | A61B 8/06 348/163 |
| 2013/0261445 A1 | 10/2013 | Ertel et al. | |
| 2014/0319317 A1* | 10/2014 | Lai | G01J 1/42 250/200 |
| 2015/0161788 A1* | 6/2015 | Ohyu | G06T 7/0016 382/131 |
| 2015/0208930 A1 | 7/2015 | Gall | |
| 2015/0250437 A1* | 9/2015 | Zaiki | A61M 5/007 600/301 |

* cited by examiner

DETERMINATION AND PRESENTATION OF FLOW TRANSIT CURVES

BACKGROUND

Contrast media are used to enhance the contrast of patient vasculature within x-ray images. For example, a contrast medium is introduced into a patient volume (e.g., via intravenous injection) and an x-ray image of the volume is acquired while the medium is located within the volume. In the x-ray image, structures which contain the medium (e.g., veins and arteries) appear darker than they would otherwise appear.

X-ray images may be successively acquired as a contrast medium passes through patient vasculature. These images portray the flow of contrast medium over time and may be displayed in rapid succession to animate the flow of contrast medium.

A transit curve may be generated based on such successively-acquired images. A transit curve depicts a normalized percentage of contrast medium concentration within a region of interest over time. However, a conventional transit curve does not differentiate between the respective contributions of contrast flow through vessels and contrast flow through other tissue within the region of interest.

BRIEF DESCRIPTION OF THE DRAWINGS

The construction and usage of embodiments will become apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments facilitate the generation of at least two transit curves depicting contrast medium concentration within a region of interest over time. One transit curve depicts contrast medium concentration within vessels of the region of interest and a second transit curve depicts contrast medium concentration within other structures of the region of interest.

According to some embodiments, image frames of a patient volume are acquired as a contrast medium passes through the volume. These image frames are used to determine pixel locations associated with blood vessels. For each image frame, a first value is determined indicating contrast medium concentration within blood vessels of a region of interest, and a second value is determined indicating contrast medium concentration within other tissues of the region of interest. For example, a first normalized sum of pixel intensities may be determined for the pixel locations associated with blood vessels, and a second normalized sum of pixel intensities may be determined for the pixel locations not associated with vessels. The normalized sums for each image are graphed with respect to time (i.e., the time associated with each image).

Figure 1:
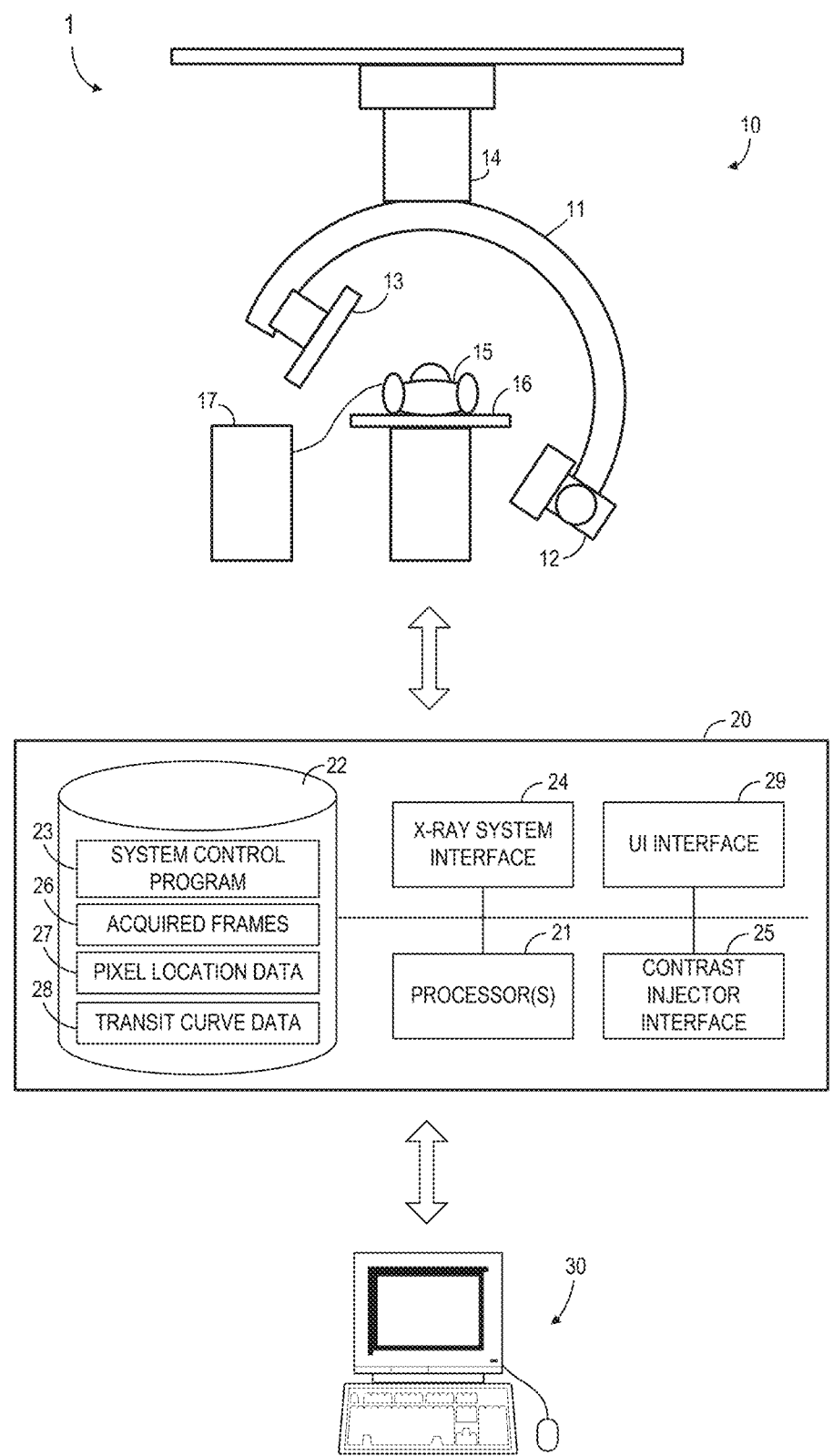
FIG. 1 illustrates a system according to some embodiments.

FIG. 1 illustrates system 1 according to some embodiments. System 1 includes x-ray imaging system 10, control and processing system 20, and operator terminal 30. Generally, and according to some embodiments, x-ray imaging system 10 introduces contrast medium into a patient volume and acquires x-ray images of the patient volume. Control and processing system 20 controls x-ray imaging system 10 and receives the acquired images therefrom. Control and processing system 20 processes the images as described below and provides transit curves to terminal 30 for display thereby. Such processing may be based on user input received by terminal 30 and provided to control and processing system 20 by terminal 30.

X-ray imaging system 10 comprises C-arm 11 on which radiation source 12 and radiation detector 13 are mounted. C-arm 11 is mounted on support 14 and is configured to translate clockwise or counter-clockwise with respect to support 14. This translation rotates radiation source 12 and radiation detector 13 around a central volume while maintaining the physical relationship therebetween. Embodiments are not limited to C-arm-based imaging systems.

Radiation source 12 may comprise any suitable radiation source, including but not limited to a Gigalix™ x-ray tube. In some embodiments, radiation source 12 emits electron, photon or other type of radiation having energies ranging from 50 to 150 keV.

Radiation detector 13 may comprise any system to acquire an image based on received x-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, radiation detector 13 converts received photons to electrical charge without requiring a scintillator layer. The photons are absorbed directly by an array of amorphous selenium photoconductors. The photoconductors convert the photons directly to stored electrical charge. Radiation detector 13 may comprise a CCD or tube-based camera, including a light-proof housing within which are disposed a scintillator, a mirror, and a camera.

The charge developed and stored by radiation detector 13 represents radiation intensities at each location of a radiation field produced by x-rays emitted from radiation source 12. The radiation intensity at a particular location of the radiation field represents the attenuative properties of mass (e.g., body tissues) lying along a divergent line between radiation source 12 and the particular location of the radiation field.

The set of radiation intensities acquired by radiation detector 13 may therefore represent a two-dimensional projection image of this mass.

Contrast injector 17 may comprise any known device or devices suitable to controllably introduce contrast medium into a patient volume. As described above, structures which contain contrast medium appear darker in x-ray images than they would otherwise appear. Contrast injector 17 may include a reservoir for each of one or more contrast media, and a patient interface such as medical-grade tubing terminating in a hollow needle.

System 20 may comprise any general-purpose or dedicated computing system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processors 21 may execute system control program 23 to move C-arm 11, to move table 16, to cause radiation source 12 to emit radiation, to control detector 13 to acquire an image, to cause injector 17 to introduce contrast medium into a volume of patient 15 and to perform any other function. In this regard, system 20 includes x-ray system interface 24 and contrast injector interface 25 for communication with corresponding units of system 10.

Images acquired from system 10 are stored in data storage device 22 as acquired frames 26, in DICOM or another data format. Acquired frames 26 may consist of, in some embodiments, two-dimensional images of a patient volume which does not include a contrast medium (i.e., mask frames) and two-dimensional images of the patient volume including a contrast medium (i.e., fill frames). Each acquired frame 26 may be further associated with details of its acquisition, including but not limited to time of acquisition, imaging plane position and angle, imaging position, radiation source-to-detector distance, patient anatomy imaged, patient position, contrast medium bolus injection profile, x-ray tube voltage, image resolution and radiation dosage.

Processor(s) 21 may further execute system control program 23 to generate pixel location data 27 and transit curve data 28, some embodiments of which will be described below. Transit curve data 28 may be provided to terminal 30 via UI interface 29 of system 20. UI interface 29 may also receive input from terminal 30, which is used to control processing of acquired frames 26 as described below.

Terminal 30 may comprise a display device and an input device coupled to system 20. Terminal 30 may display acquired frames 26 and/or transit curve data 28 received from system 20 and may receive user input for controlling display of the images, operation of imaging system 10, and/or the processing of acquired frames 26. In some embodiments, terminal 30 is a separate computing device such as, but not limited to, a desktop computer, a laptop computer, a tablet computer, and a smartphone.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Moreover, system 20 receives input from terminal 30 and provides processed images and/or transit curves to terminal 30. Embodiments are not limited to a single system performing each of these functions. For example, system 10 may be controlled by a dedicated control system, with the acquired frames being provided to a separate image processing system over a computer network or via a physical storage medium (e.g., a DVD).

Figure 2:
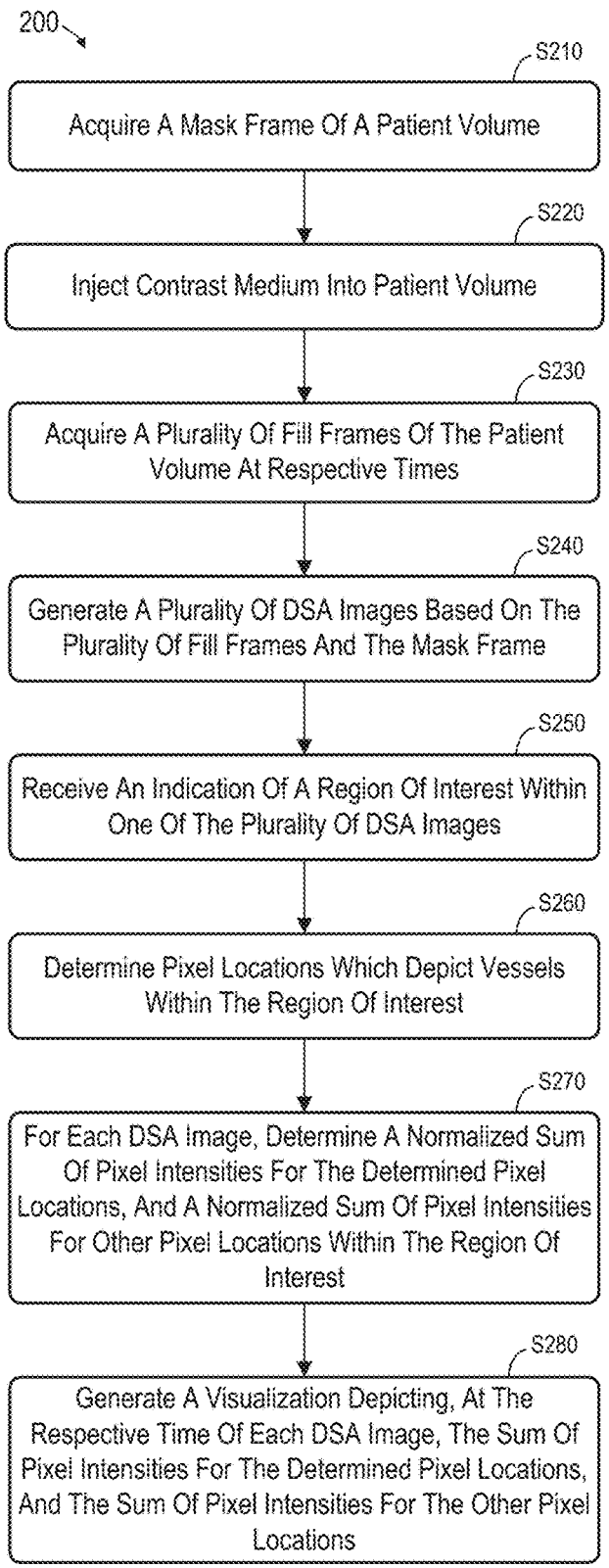
FIG. 2 is a flow diagram of process to generate a graph according to some embodiments.

FIG. 2 is a flow diagram of process 200 according to some embodiments. Process 200 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. Examples of these processes will be described below with respect to the elements of system 1, but embodiments are not limited thereto.

It will be assumed that, prior to S210, the patient is positioned for imaging according to known techniques. For example, and with reference to the elements of system 1, patient 15 is positioned on table 16 to place a particular volume of patient 15 between radiation source 12 and radiation detector 13. System 20 may assist in adjusting table 16 to position the patient volume as desired. As is known in the art, such positioning may be based on a location of a volume of interest, on positioning markers located on patient 15, on a previously-acquired planning image, and/or on a portal image acquired after an initial positioning of patient 15 on table 16.

According to some embodiments, a mask frame is acquired at a desired projection angle at S210. The mask frame is acquired before introduction of a contrast medium into the patient volume. In some embodiments of S210, radiation source 12 is powered by a high-powered generator to emit x-ray radiation toward radiation detector 13 at the desired projection angle. The parameters of the x-ray radiation emission (e.g., timing, x-ray tube voltage, dosage) may be controlled by system control program 23 as is known in the art. Radiation detector 13 receives the emitted radiation and produces a set of data (i.e., a projection image). The projection image may be received by system 20 and stored among acquired frames 26 in either raw form or after any suitable pre-processing (e.g., denoising filters, median filters and low-pass filters).

Next, at S220, contrast medium is injected into the patient volume (e.g., into an artery of the patient volume). According to some embodiments of S220, system 20 instructs contrast injector 17 to introduce contrast medium into an artery of patient 15. The parameters of the medium introduction (e.g., flow rate, location, volume) may be controlled by system control program 23 as is known in the art.

A plurality of fill frames of the patient volume are acquired at S230. The fill frames are acquired from the same projection angle as was used during acquisition of the mask frame. Each of the plurality of fill frames is acquired at a respective time, such that each fill frame shows the injected contrast medium within the patient volume at a different time. Viewed as a whole, the fill frames illustrate movement of the contrast medium through the patient volume over time.

Figure 3:
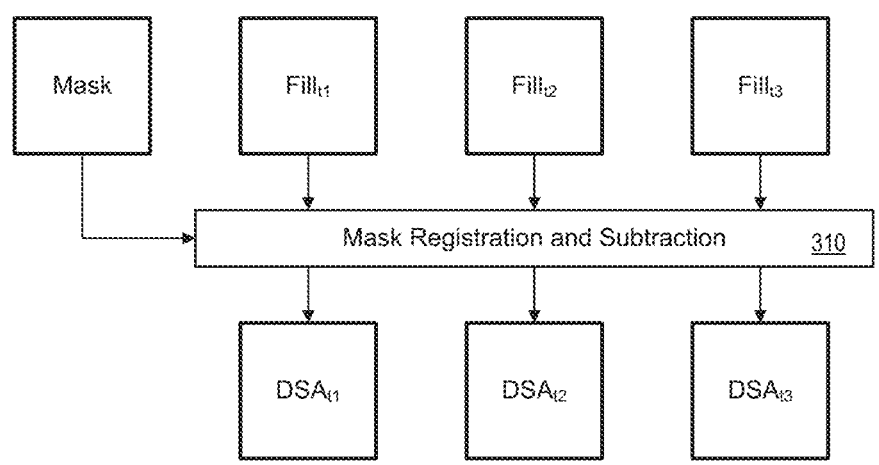
FIG. 3 illustrates a portion of a process according to some embodiments.

Next, at S240, a plurality of Digital Subtraction Angiography (DSA) images are generated based on the mask frame and the fill frame. FIG. 3 illustrates generation of DSA images at S240 according to some embodiments. A mask frame acquired at S210 is depicted along with three fill frames ($Fill_{f1}$, $Fill_{f2}$, $Fill_{f3}$) acquired at respective times during S230. For the present example, it is assumed that fill frame $Fill_{f1}$ was acquired at time t1, fill frame $Fill_{f2}$ was acquired at time t2, and fill frame Fill$_{t3}$ was acquired at time t3. Embodiments are not limited to three fill frames.

S240 may commence by registering each of the plurality of fill frames against the mask frame. Registration is intended to remove motion artifacts between the frames, by correcting for any relative motion of the patient between acquisitions of the frames. Any motion correction technique may be employed at S240. As shown in FIG. 3, fill frames Fill$_{t1}$, Fill$_{t2}$ and Fill$_{t3}$ may be registered against the mask frame by mask registration and subtraction module 310 (e.g., processor-executable software code executed by computing hardware) as illustrated.

Next, the mask frame is subtracted from each of the registered fill frames as in known in the art, resulting in DSA images DSA$_{t1r}$, DSA$_{t2r}$ and DSA$_{t3r}$. Since the mask frame depicts anatomical structures without contrast medium and the fill frames Fill$_{t1}$, Fill$_{t2}$, Fill$_{t3}$, depict anatomical structures and contrast medium, the DSA images depict, substantially, contrast medium without the structures depicted in the mask image.

Figure 4:
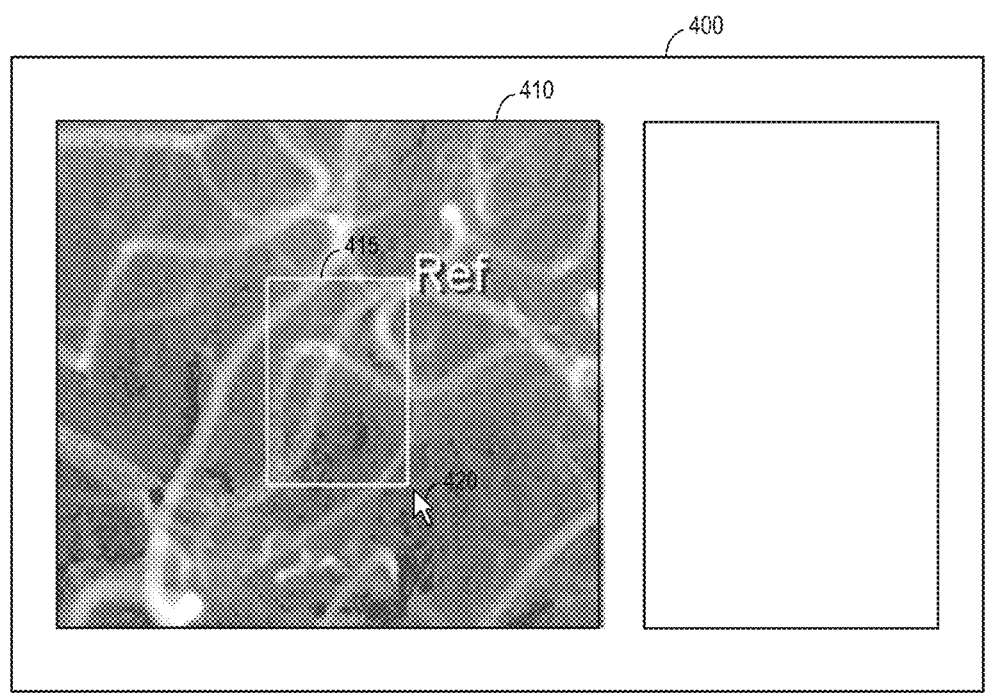
FIG. 4 is an outward view of a user interface to define a region of interest according to some embodiments.

A region of interest is determined at S250. According to some embodiments, an one of the DSA images is presented to an operator, who selects a region of the DSA image. FIG. 4 illustrates user interface 400 which may be displayed on a display of system 30 according to some embodiments. Region 410 of user interface 400 includes a DSA image showing contrast medium within a patient volume at a particular time. Region 410 may display the plurality of generated DSA images in succession so as to present an animation of contrast medium flow through the depicted patient volume.

FIG. 4 also shows selection graphic 415 which circumscribes a region of interest. Graphic 415 may have been drawn by an operator via manipulation of cursor 420 (e.g., using a "click and drag" input metaphor). According to some embodiments, the contrast medium is present in both vessel structures and other structures (e.g., capillaries) within the region of interest in at least one of the DSA images. Any known system to select a region of an image may be employed in S250.

Pixel locations which depict vessels within the region of interest are determined at S260. S260 results in the generation of data identifying pixel locations which correspond with vessel locations and pixel locations which correspond with non-vessel tissue location. Accordingly, in some embodiments, S260 includes determination of first pixel locations which depict non-vessel tissue within the region of interest, after which second pixel locations which depict vessels are determined based on the first pixel locations.

Figure 5:
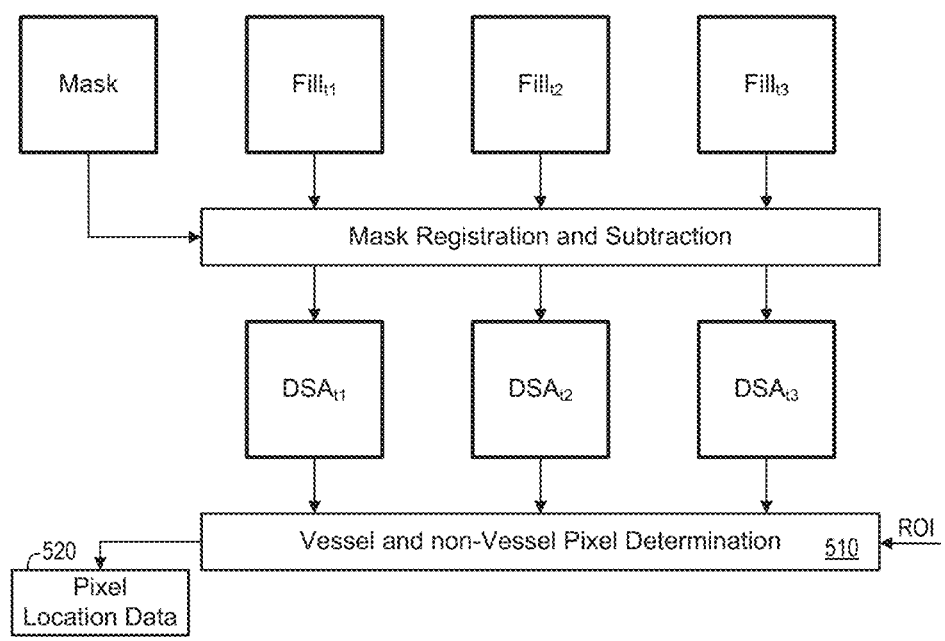
FIG. 5 illustrates a portion of a process according to some embodiments.

FIG. 5 illustrates vessel and non-vessel determination module 510 for determining pixel location data 520 based on one or more DSA images and a defined region of interest in some embodiments. Pixel location data 520 may specify, for each pixel location in the region of interest, whether the pixel location corresponds to vessels or non-vessel structures.

Figures 6A, 6B:
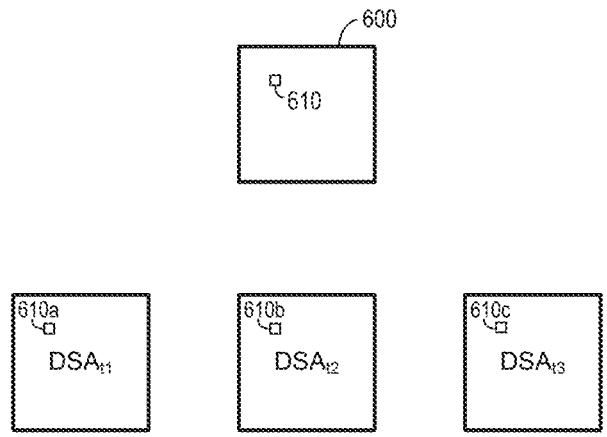
FIG. 6A illustrates pixel locations according to some embodiments.
FIG. 6B illustrates pixel location data according to some embodiments.

FIG. 6A shows dummy frame 600 to illustrate the concept of "pixel location" as used herein. Frame 600 shares the dimensions and pixel density, and therefore the same pixel locations, as each of DSA images DSA$_{t1r}$, DSA$_{t2r}$ and DSA$_{t3r}$. Pixel location 610 corresponds to pixel locations 610a, 610b and 610c of DSA images DSA$_{t1r}$, DSA$_{t2r}$ and DSA$_{t3r}$, respectively. Each of DSA images DSA$_{t1r}$, DSA$_{t2r}$ and DSA$_{t3r}$, includes a pixel at respective pixel locations 610a, 610b and 610c, and each of those pixels is associated with a pixel value.

Accordingly, for each pixel location (e.g., location 610) in the region of interest, S260 identifies whether or not the pixels at corresponding locations (e.g., locations 610a, 610b and 610c) of the DSA images represent a vessel. Table 650, in FIG. 6B, may comprise an implementation of pixel location data 520, but embodiments are not limited thereto. Any number or type of data structures suitable for relating the data described herein may be employed. Each row of table 650 includes a pixel location and a location type. According to some embodiments of S260, one row of table 650 is generated and populated for each pixel location of the region of interest.

According to some embodiments, S260 comprises applying a band-pass filter to one of the DSA images to generate a filtered image which includes only structures that are the size of the vessels. For a typical image having 1024×1024 pixel resolution, a bandpass filter according to some embodiments preserves structures from 3 to 40 pixels wide. In other embodiments, the bandpass filter preserves a different range of structure size based on the physical size of the object being removed and the resolution of the image being used.

The resultant band-pass filtered image data may be compared to a threshold to generate a threshold image $I_T$, where $I_T(x,y)=1$ if the gray level of the band-pass image is greater than the threshold, and of 0 value if not. The pixels of $I_T$ which equal 1 are determined to correspond to vessel pixel locations. The threshold may comprise a specific gray value or may be automatically selected based on a histogram analysis of an image showing a significant amount of contrast a medium-filled vasculature to separate the vessels from the background.

At S270, an indicator of contrast medium concentration within the vessel pixel locations of the region of interest is determined for each DSA image. Also, for each DSA image, an indicator of contrast medium concentration within the other pixel locations of the region of interest is determined. According to some embodiments, the indicator is a normalized sum of pixel intensities. For example, the pixel intensities of each vessel pixel location within the region of interest are summed, for each DSA image. The largest sum is designated as representing 100% concentration and the other sums are normalized to the largest sum. This determination is repeated for the non-vessel pixel locations, with the sums being normalized to the largest sum of the vessel pixel locations. Indicators of contrast medium concentration within vessel and non-vessel pixel locations may be determined by any other method according to some embodiments.

Figure 7:
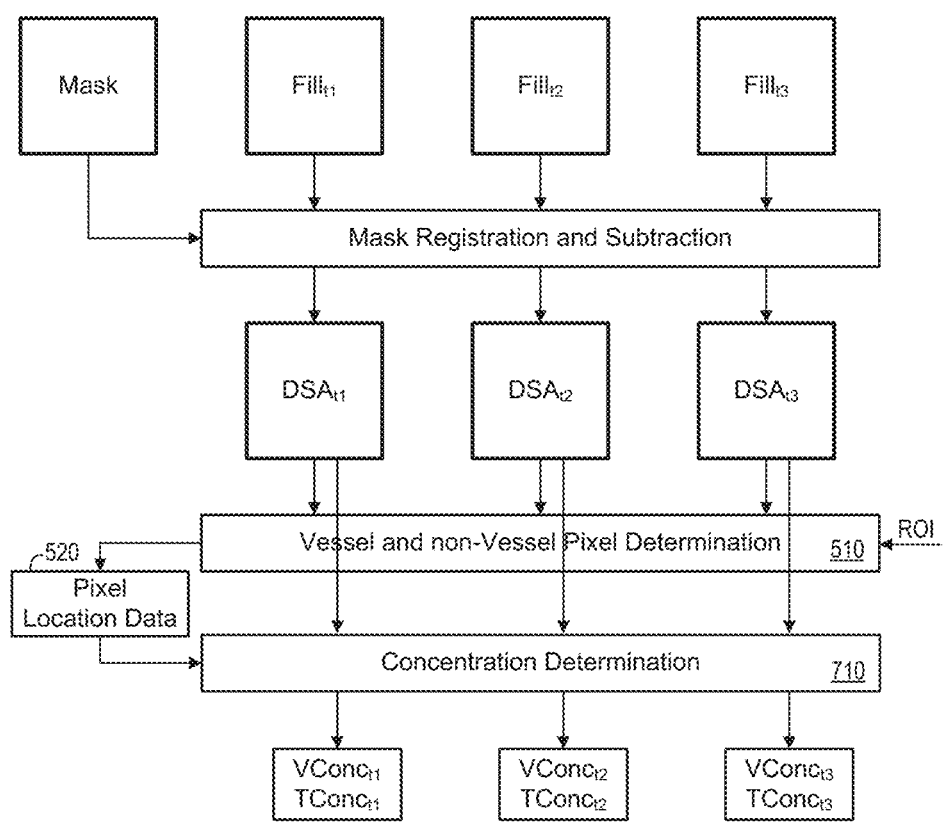
FIG. 7 illustrates a portion of a process according to some embodiments.

FIG. 7 illustrates concentration determination module 710 to determine contrast medium concentrations for vessel and non-vessel pixel locations of each of DSA images DSA$_{t1}$, DSA$_{t2}$, and DSA$_{t3}$ according to some embodiments. As shown, module 710 uses pixel location data 520 to determine the contrast medium concentration within vessel pixel locations (i.e., V$_{conc}$) and within non-vessel pixel locations (i.e., T$_{conc}$) for each of DSA images DSA$_{t1}$, DSA$_{t2}$, and DSA$_{t3}$.

Next, at S280, a visualization is generated which depicts, at the respective time of each DSA, the determined contrast medium concentrations within vessel pixel locations and within non-vessel pixel locations. According to the present example, the generated visualization depicts, for the respective time of each DSA, the normalized sum of pixel intensities for the vessel pixel locations in the region of interest, and the normalized sum of pixel intensities for non-vessel pixel locations in the region of interest.

Figure 8:
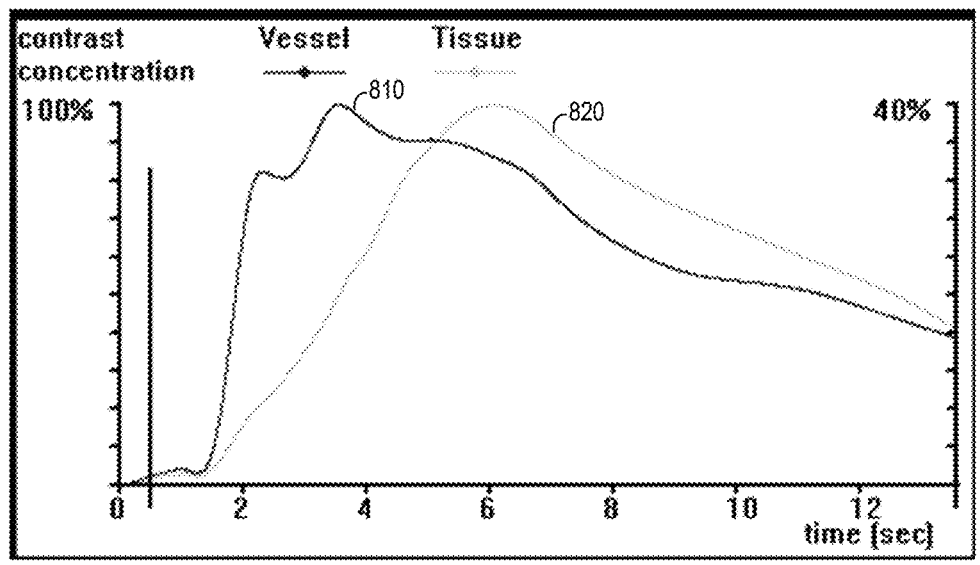
FIG. 8 illustrates a graph generated according to some embodiments.

FIG. 8 illustrates a visualization which may be generated at S280 according to some embodiments. The x-axis represents the acquisition time of the DSA images from which corresponding plotted data is determined. The left-most y-axis represents a scale of contrast medium concentration within vessel pixel locations which governs transit curve 810. Transit curve 820 has been scaled to substantially match the peak value of transit curve 810, to improve readability. Accordingly, the right-most y-axis represents a scale of contrast medium concentration within non-vessel pixel locations of the region of interest. One use of the visualization would be to compare pre- and post-intervention transit curves of the same region of interest to demonstrate the efficacy of treatment.

Figure 9:
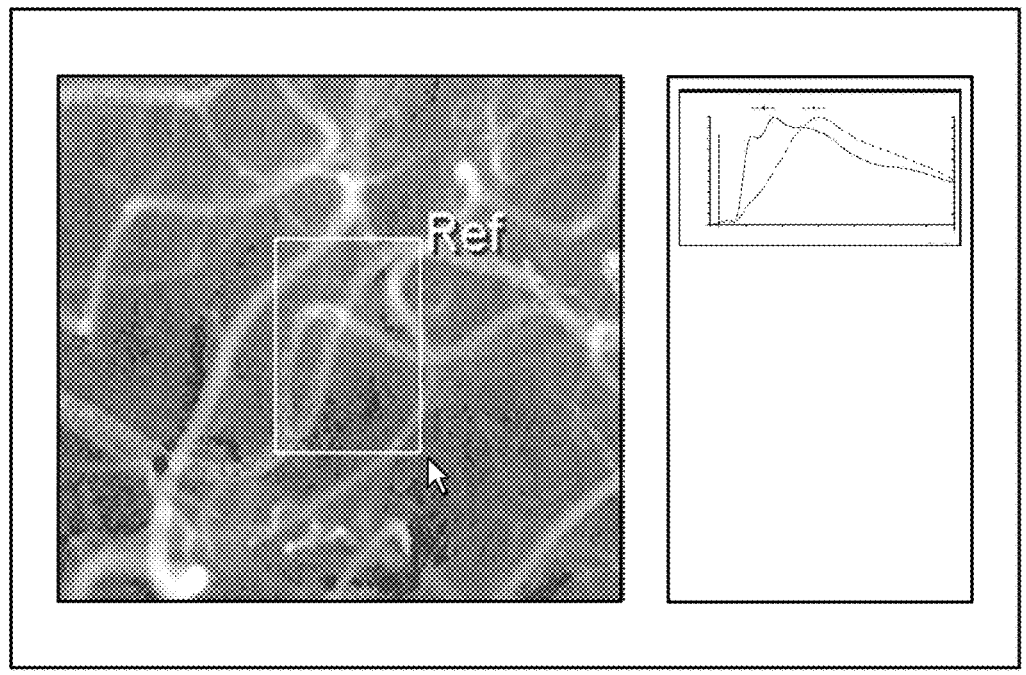
FIG. 9 is an outward view of a user interface according to some embodiments.

FIG. 9 illustrates a user interface displayed, for example, on a display of terminal 30 according to some embodiments. In some embodiments, the DSA images $DSA_{t1}$, $DSA_{t2}$ and $DSA_{t3}$ may be displayed in succession along with an indication of the region of interest to animate the flow of contrast medium therein. As shown in FIG. 9, the user interface may simultaneously display a corresponding visualization such as the FIG. 8 visualization. According to some embodiments, data points (i.e., determined contrast medium concentrations) of the visualization which correspond to a DSA image may be highlighted within the visualization when the corresponding DSA image is displayed in the user interface.

According to some embodiments, the determination at S260 may be performed prior to receiving an indication of a region of interest. For example, pixel location data for all pixel locations may be determined after S240 but before S250.

Known processing techniques may be applied to the DSA images to remove noise, adjust brightness, collimate the field of view, and/or conform the frames to the display properties of the display device of terminal 30.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
   an X-ray detector and an X-ray source operable to:
     acquire a plurality of image frames of a patient volume, each of the plurality of image frames depicting a contrast medium within the patient volume at a respective time;
   a processor to:
     receive an indication of a region of interest of the image frames;
     determine a first set of pixel locations of the region of interest which depict blood vessels;
     determine a second set of pixel locations of the region of interest which depict tissue which does not include blood vessels and in which contrast medium is present;
     for each of the plurality of the image frames, determine a first contrast medium concentration corresponding to the first set of pixel locations;
     for each of the plurality of the image frames, determine a second contrast medium concentration corresponding to the second set of pixel locations; and
   a display to display a visualization depicting a first contrast medium concentration and a second contrast medium concentration with respect to the respective time of each of the plurality of the image frames.

2. A system according to claim 1, wherein determination of the first contrast medium concentration corresponding to the first set of pixel locations comprises summing pixel intensities of pixels located at the first set of pixel locations of the one of the image frames, and
   wherein determination of the second contrast medium concentration corresponding to the second set of pixel locations comprises summing pixel intensities of pixels located at the second set of pixel locations of the one of the image frames.

3. A system according to claim 1, wherein the visualization comprises a first curve depicting the first contrast medium concentration with respect to time and a second curve depicting the second contrast medium concentration with respect to time, and
   wherein the first curve and the second curve are normalized to a peak value of the first curve.

4. A system according to claim 1, wherein determination of the first set of pixel locations comprises application of a band-pass filter to one of the images to generate a filtered image which includes only structures that are the size of blood vessels.

5. A system comprising:
   an interface to:
     receive a plurality of image frames of a patient volume, each of the plurality of image frames depicting a contrast medium within the patient volume at a respective time;
   a processor to:
     determine a first set of pixel locations of the image frames which depict blood vessels;
     determine a second set of pixel locations of the image frames which depict tissue which does not include blood vessels and in which contrast medium is present;
     for one of the image frames, determine a first contrast medium concentration corresponding to the first set of pixel locations;
     for one of the image frames, determine a second contrast medium concentration corresponding to the second set of pixel locations; and
   a display to display a visualization depicting the first contrast medium concentration and the second contrast medium concentration with respect to the respective time of the one of the image frames.

6. A system according to claim 5, further comprising:
   an X-ray detector and an X-ray source operable to acquire the plurality of image frames.

7. A system according to claim 6, further comprising a contrast injector to inject the contrast medium into the patient volume.

8. A system according to claim 5, wherein determination of the first contrast medium concentration corresponding to the first set of pixel locations comprises summing pixel intensities of pixels located at the first set of pixel locations of the one of the image frames, and
   wherein determination of the second contrast medium concentration corresponding to the second set of pixel locations comprises summing pixel intensities of pixels located at the second set of pixel locations of the one of the image frames.

9. A system according to claim 8, wherein determination of the first contrast medium concentration corresponding to the first set of pixel locations for the one of the image frames comprises determination of the first contrast medium concentration corresponding to the first set of pixel locations for each of the plurality of the image frames, wherein determination of the second contrast medium concentration corresponding to the second set of pixel locations for the one of the image frames comprises determination of the second contrast medium concentration corresponding to the second set of pixel locations for each of the plurality of the image frames, and wherein the visualization depicts a first contrast medium concentration and a second contrast medium concentration with respect to the respective time of each of the plurality of the image frames.

10. A system according to claim 9, wherein the visualization comprises a first curve depicting the first contrast medium concentration with respect to time and a second curve depicting the second contrast medium concentration with respect to time.

11. A system according to claim 5, wherein determination of the first contrast medium concentration corresponding to the first set of pixel locations for the one of the image frames comprises determination of the first contrast medium concentration corresponding to the first set of pixel locations for each of the plurality of the image frames, wherein determination of the second contrast medium concentration corresponding to the second set of pixel locations for the one of the image frames comprises determination of the second contrast medium concentration corresponding to the second set of pixel locations for each of the plurality of the image frames, and wherein the visualization depicts a first contrast medium concentration and a second medium concentration with respect to the respective time of each of the plurality of the image frames.

12. A system according to claim 11, wherein the visualization comprises a first curve depicting the first contrast medium concentration with respect to time and a second curve depicting the second contrast medium concentration with respect to time.

13. A system according to claim 5, wherein determination of the first set of pixel locations comprises application of a band-pass filter to one of the images to generate a filtered image which includes only structures that are the size of blood vessels.

14. A system according to claim 13, wherein determination of the first contrast medium concentration corresponding to the first set of pixel locations for the one of the image frames comprises determination of the first contrast medium concentration corresponding to the first set of pixel locations for each of the plurality of the image frames, wherein determination of the second contrast medium concentration corresponding to the second set of pixel locations for the one of the image frames comprises determination of the second contrast medium concentration corresponding to the second set of pixel locations for each of the plurality of the image frames, and wherein the visualization comprises a first curve depicting the first contrast medium concentration with respect to time and a second curve depicting the second contrast medium concentration with respect to time.

15. A method comprising:

receiving a plurality of image frames of a patient volume, each of the plurality of image frames depicting a contrast medium within the patient volume at a respective time;

determining a first set of pixel locations of the image frames which depict blood vessels;

determining a second set of pixel locations of the image frames which depict tissue which does not include blood vessels and in which contrast medium is present;

for one of the image frames, determining a first contrast medium concentration corresponding to the first set of pixel locations;

for one of the image frames, determining a second contrast medium concentration corresponding to the second set of pixel locations; and displaying a visualization depicting the first contrast medium concentration and the second contrast medium concentration with respect to the respective time of the one of the image frames.

16. A method according to claim 15, wherein determining the first contrast medium concentration corresponding to the first set of pixel locations comprises summing pixel intensities of pixels located at the first set of pixel locations of the one of the image frames, and wherein determining the second contrast medium concentration corresponding to the second set of pixel locations comprises summing pixel intensities of pixels located at the second set of pixel locations of the one of the image frames.

17. A method according to claim 16, wherein determining the first contrast medium concentration corresponding to the first set of pixel locations for the one of the image frames comprises determining the first contrast medium concentration corresponding to the first set of pixel locations for each of the plurality of the image frames, wherein determining the second contrast medium concentration corresponding to the second set of pixel locations for the one of the image frames comprises determining the second contrast medium concentration corresponding to the second set of pixel locations for each of the plurality of the image frames, and wherein the visualization depicts a first contrast medium concentration and a second contrast medium concentration with respect to the respective time of each of the plurality of the image frames.

18. A method according to claim 15, wherein determining the first contrast medium concentration corresponding to the first set of pixel locations for the one of the image frames comprises determining the first contrast medium concentration corresponding to the first set of pixel locations for each of the plurality of the image frames, wherein determining the second contrast medium concentration corresponding to the second set of pixel locations for the one of the image frames comprises determining the second contrast medium concentration corresponding to the second set of pixel locations for each of the plurality of the image frames, and wherein the visualization comprises a first curve depicting the first contrast medium concentration with respect to time and a second curve depicting the second contrast medium concentration with respect to time.

19. A method according to claim 15, wherein determining the first set of pixel locations comprises applying a band-pass filter to one of the images to generate a filtered image which includes only structures that are the size of blood vessels.

* * * * *